US00PP20436P2

(12) United States Plant Patent
Caster et al.

(10) Patent No.: US PP20,436 P2
(45) Date of Patent: Oct. 20, 2009

(54) BLUEBERRY PLANT NAMED 'DRISBLUETHREE'

(50) Latin Name: *Vaccinium corymbosum*
Varietal Denomination: DrisBlueThree

(75) Inventors: Brian Caster, Watsonville, CA (US); Arlen Draper, Payson, AZ (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/082,272

(22) Filed: Apr. 10, 2008

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu
(74) *Attorney, Agent, or Firm*—Jondle & Associates, P.C.

(57) ABSTRACT

This invention relates to a new and distinct cultivar of blueberry plant primarily characterized by medium-large berries with strong sweetness, weak acidity, and a nearly spherical berry shape and berries that have green flesh, is disclosed.

2 Drawing Sheets

Genus and species: *Vaccinium corymbosum.*
Variety denomination: 'DrisBlueThree'.

BACKGROUND OF THE NEW PLANT

The present invention relates to a new and distinct blueberry cultivar designated 'DrisBlueThree' and botanically known as *Vaccinium corymbosum*. This new blueberry cultivar was discovered in Watsonville, Santa Cruz County, Calif. in September 2000 as a result of a hybridization between the female parent, 'FL98-11' an unpatented variety and the male parent, 'FL89-152' an unpatented variety. The female and male parents are no longer available for comparison with the instant plant.

The original seedling of the new cultivar was asexually propagated at a nursery in Watsonville, Monterey, Calif. 'DrisBlueThree' was subsequently asexually propagated and underwent further testing at a nursery in Watsonville, Santa Cruz County, Calif. for seven years. 'DrisBlueThree' has been asexually propagated via softwood cuttings. The present invention has been found to be stable and reproduce true to type through successive asexual propagations.

SUMMARY OF THE INVENTION

The following are the most outstanding and distinguishing characteristics of this new cultivar when grown under normal horticultural practices in Watsonville, Santa Cruz County, Calif.

1. Medium-large berries with strong sweetness;
2. Weak acidity and a nearly spherical berry shape; and
3. Berries that have green flesh.

DESCRIPTION OF THE PHOTOGRAPHS

The accompanying color photographs show typical specimens of the new cultivar at various stages of development as nearly true as it is possible to make in color reproductions. The photographs are of plants that are 7 years old.

DESCRIPTION OF THE NEW CULTIVAR

Figure 1:
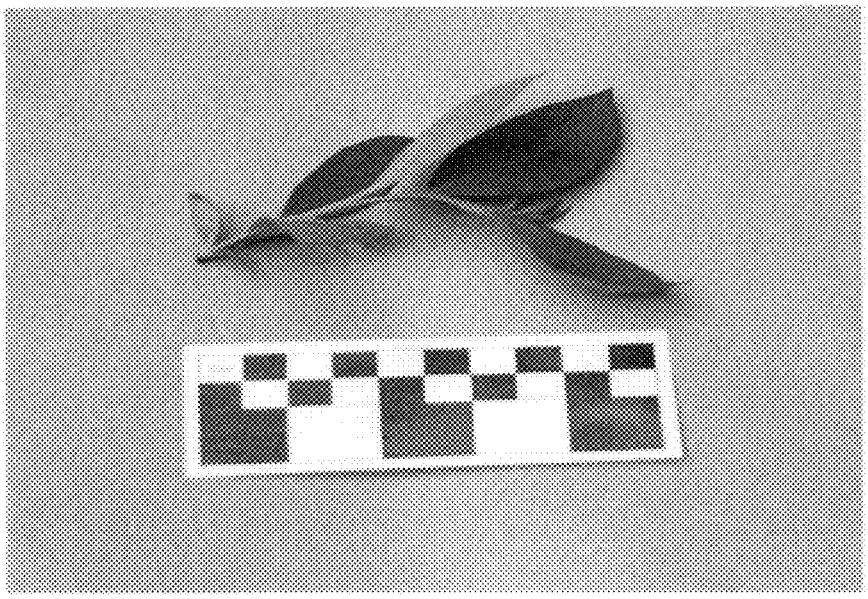
FIG. 1 shows a leaf cluster.
Figure 2:
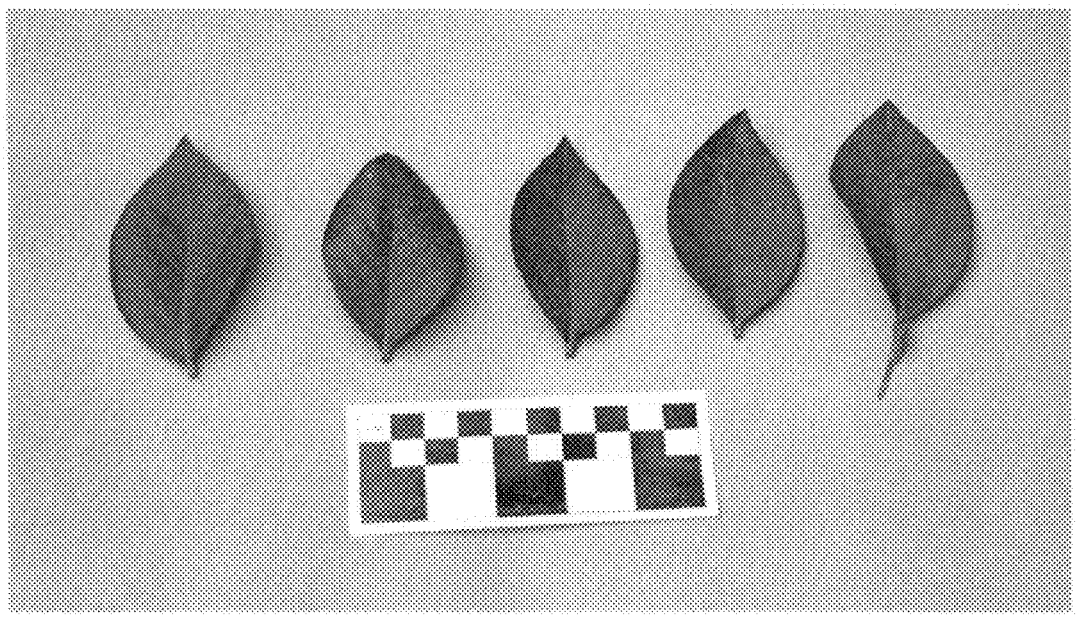
FIG. 2 shows a close-up of the upper surface of the leaves.
Figure 3:
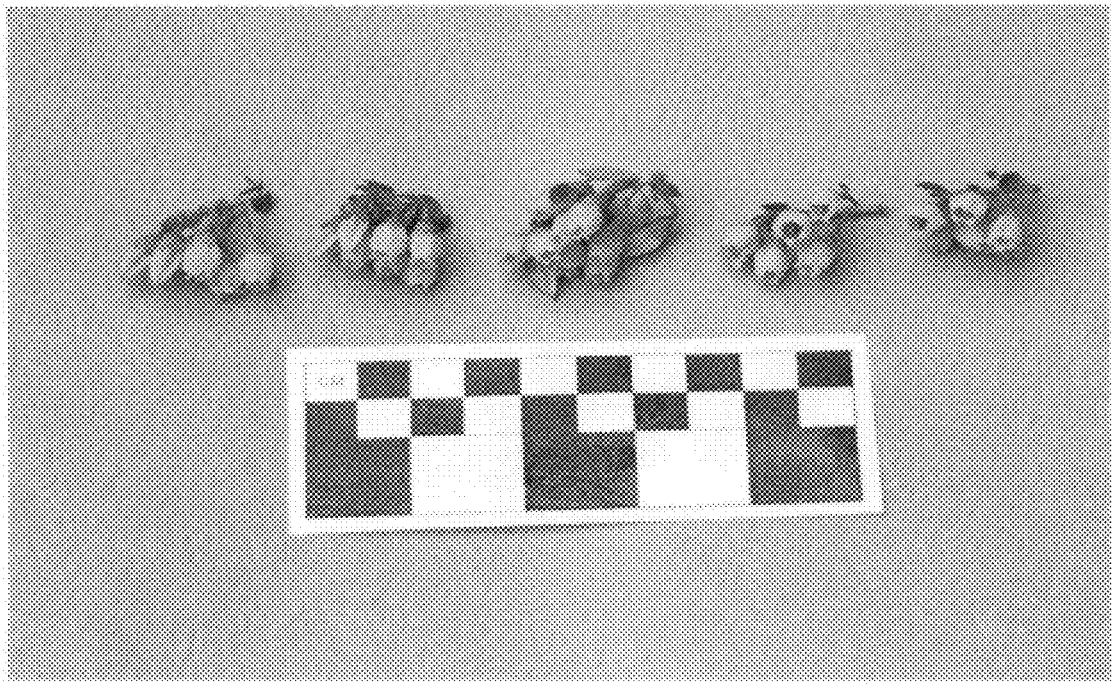
FIG. 3 shows the mature flowers.
Figure 4:
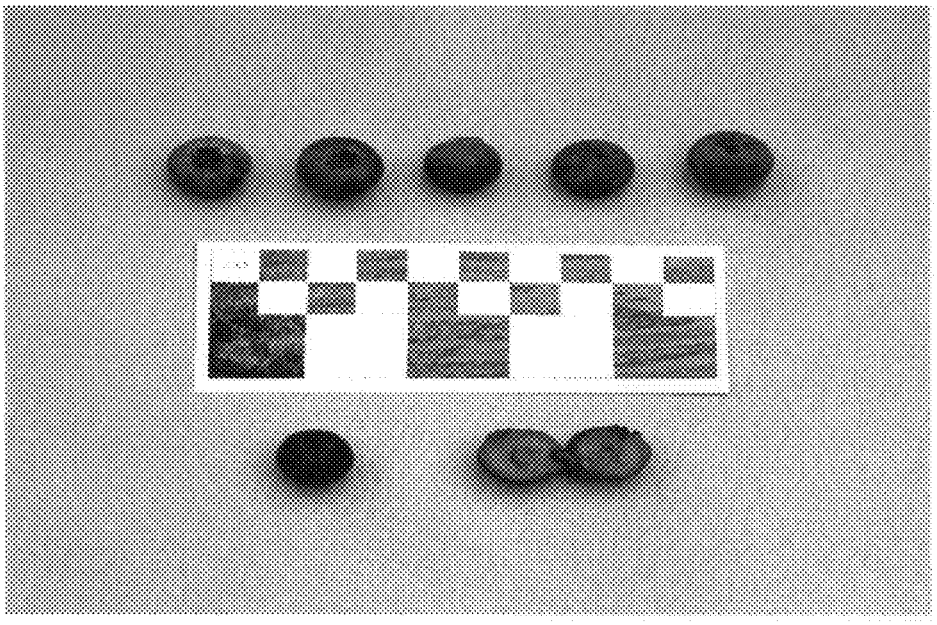
FIG. 4 shows the whole fruit and a longitudinal-section of the fruit.

The following description of 'DrisBlueThree' is based on observations taken from the 2007 growing season in Watsonville, Santa Cruz County, Calif., where the age of the 'DrisBlueThree' plants was 7 years, while the age of the O'Neal plants were 12 years old. All descriptions are in accordance with UPOV terminology. Color designations, color descriptions, and other phenotypical descriptions may deviate from the stated values and descriptions depending upon variation in environmental, seasonal, climatic and cultural conditions. 'DrisBlueThree' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of blueberry plant 'O'Neal' (unpatented). Table 1 includes plant, canopy and cane characteristics.

TABLE 1

| Characteristic | 'DrisBlueThree' | 'O'Neal' |
|---|---|---|
| Plant: | | |
| Vigor | Strong | Low |
| Growth habit | Strongly erect shrub | Bushy |
| Chilling requirement | Low | Medium |
| Propagation | Softwood cuttings | Softwood cuttings |
| Age | 7 years | 12 years |
| Canopy: | | |
| Bush height (cm) | 126 | 134 |
| Canopy width (cm) | 109 | 124 |
| Height/Width ratio | 1.2 | 1.1 |

TABLE 1-continued

| Characteristic | 'DrisBlueThree' | 'O'Neal' |
|---|---|---|
| Canes: | | |
| Age at maturity (years) | 3 years | 3 years |
| Mature cane texture | Rough | Rough |
| Mature cane diameter (cm) | 0.864 cm | .734 |
| Mature cane length (cm) | 83 cm | 69.0 |
| Mature cane color | RHS 146C (yellow-green) | RHS 138A (green) |
| Cane renewal | Strong | Weak |

Table 2 shows plant characteristics of the new variety compared with plant characteristics of blueberry plant 'O'Neal' (unpatented). Table 2 includes bud, calyx, corolla, flower and pedicel characteristics. Where "n/a" appears for a characteristic, it indicates a characteristic is not available.

TABLE 2

| Characteristic | 'DrisBlueThree' | 'O'Neal' |
|---|---|---|
| Bud: | | |
| Time of bud break | Early | Early |
| Flowers per bud | 7 | 6 |
| Calyx: | | |
| Diameter at anthesis (cm) | 0.52 | 0.658 |
| Lobe count | 5 | 5 |
| Color | RHS 138B (medium green) | RHS 145C (light yellow-green) |
| Corolla: | | |
| Petals, general | Fused into a corolla with 5 lobes | Fused into a corolla with 5 lobes |
| Length (cm) | 0.936 | 1.014 |
| Diameter (cm) | 0.614 | 0.886 |
| Aperature diameter (cm) | 0.316 | 0.334 |
| Mature color | RHS 157B (white) | RHS 155A (white) |
| Flower: | | |
| Type | Perfect hypogynous (inferior ovary); stamens attached at base of fused corolla tube | Perfect hypogynous (inferior ovary); stamens attached at base of fused corolla tube |
| Shape | Urceolate | Urceolate |
| Fragrance | Faint | Very faint |
| Size | Small | Medium |
| 50% anthesis (full bloom) | March 15$^{th}$ | n/a |
| 1% bloom | Early | Early |
| Pedicel: | | |
| Color | RHS N144C (yellow-green) | RHS 144D (light yellow-green) |
| Length (cm) | 0.892 | 0.478 |

Table 3 shows plant characteristics of the new variety compared with plant characteristics of blueberry plant 'O'Neal' (unpatented). Table 3 includes leaf and shoot characteristics.

TABLE 3

| Characteristic | 'DrisBlueThree' | 'O'Neal' |
|---|---|---|
| Leaves: | | |
| Arrangement | Alternate | Alternate |
| Shape | Simple and elliptic | Simple and broadly elliptic to slightly ovate |
| Apex | Broadly acuminate | Broadly acute |

TABLE 3-continued

| Characteristic | 'DrisBlueThree' | 'O'Neal' |
|---|---|---|
| Base | Broadly acute | Broadly acute to slightly cuneate |
| Margin | Entire | Entire |
| Pubescence (both surfaces) | Glabrous | Glabrous |
| Length (cm) | 8.56 | 0.662 |
| Width (cm) | 3.82 | 0.344 |
| Length/width ratio | 2.2 | 1.9 |
| Color, abaxial | RHS 191B (greyed-green) | RHS 138 (green) |
| Color, adaxial | RHS 139A (green) | RHS 137A (green) |
| Venation | Reticulate | Reticulate |
| Petiole: | | |
| Length (cm) | 0.41 | 0.40 |
| Color | RHS 145B (yellow-green) | RHS N144D (yellow-green) |
| Shoots: | | |
| Internode length (cm) | 1.77 | 1.634 |

Table 4 shows plant characteristics of the new variety compared with plant characteristics of blueberry plant 'O'Neal' (unpatented). Table 4 includes berry, skin, peduncle and seed characteristics.

TABLE 4

| Characteristic | 'DrisBlueThree' | 'O'Neal' |
|---|---|---|
| Berry: | | |
| Shape | Nearly spherical | Slightly oblate sphere |
| Size | Medium | Medium |
| Weight (g) | 1.5 | 1.39 |
| Height (cm, pedicel scar to calyx) | 1.444 | 1.284 |
| Diameter (cm at equator) | 1.594 | 1.508 |
| Height/diameter ratio | 0.91 | 0.85 |
| Firmness | Very firm | Medium firm |
| Sweetness | Strong | Strong |
| Acidity | Weak | Mild |
| Season/timing (25% ripe) | Early season | Early season |
| Season/timing (50% ripe) | May 30th | June 14$^{th}$ |
| Pedicel scar diameter (cm) | 0.142 | 0.16 |
| Skin: | | |
| Bloom deposition | Heavy | Medium |
| Mature color with bloom | RHS 98D (blue) | RHS 98C (violet-blue) |
| Mature color without bloom | RHS 103A (blue) | RHS 103A (blue) |
| Immature color with bloom | RHS 191B (green) | RHS 143D (light green) |
| Flesh: | | |
| Color | RHS 145C (green) | RHS 157A (green-white) |
| Seed: | | |
| Abundance | 47 per fruit | 27 per fruit |
| Color | RHS 165A (orange-brown) | RHS 165B (greyed-orange) |
| Length (cm) | 0.148 | 0.200 |
| Width (cm) | 0.1260 | 0.112 |
| Length/width ratio | 1.17 | 1.79 |

Table 5 shows plant characteristics of the new variety compared with plant characteristics of blueberry plant 'O'Neal' (unpatented). Table 5 includes the reproductive organs.

TABLE 5

| Characteristic | 'DrisBlueThree' | 'O'Neal' |
|---|---|---|
| Reproductive Organs: | | |
| Pollination requirement | Believed to be self-fertile | |
| Ovary color | RHS 188A (greyed-green) | RHS 133C (green) |
| Pollen color | RHS 11C (yellow) | RHS 8D (light yellow) |
| Anther color | RHS 22A (yellow-orange) | RHS N170A (greyed-orange) |

TABLE 5-continued

| Characteristic | 'DrisBlueThree' | 'O'Neal' |
|---|---|---|
| Style length, including stigma (cm) | 0.86 cm | 0.810 cm |

Resistance to diseases and insects: Disease and insect resistance are typical of blueberry plants.

We claim:

1. A new and distinct cultivar of blueberry plant as described and shown herein.

* * * * *